United States Patent [19]

Marwood

[11] 4,063,638
[45] Dec. 20, 1977

[54] DIRECT DISPENSING PACKAGING OF SURGICAL SUTURES

[75] Inventor: Ronald Keith Marwood, Dorion, Canada

[73] Assignee: American Cyanamid Company, Stamford, Conn.

[21] Appl. No.: 778,190

[22] Filed: Mar. 16, 1977

[51] Int. Cl.² .............................................. A61L 17/02
[52] U.S. Cl. .................................. 206/63.3; 206/363; 206/227; 128/335.5; 206/628
[58] Field of Search ...................... 206/63.3, 363, 227, 206/498; 229/51 TS; 128/335.5

[56] References Cited

U.S. PATENT DOCUMENTS

| | | | |
|---|---|---|---|
| 3,206,018 | 9/1965 | Lewis et al. | 206/63.3 |
| 3,280,971 | 10/1966 | Regan, Jr. | 206/63.3 |
| 3,363,751 | 1/1968 | Shave et al. | 206/63.3 |
| 3,444,994 | 5/1969 | Kaepernik et al. | 206/63.3 |
| 3,487,917 | 1/1970 | Shave et al. | 206/63.3 |
| 3,857,484 | 12/1974 | Thyen | 206/63.3 |
| 3,876,068 | 4/1975 | Sonnino | 206/63.3 |
| 3,910,410 | 10/1975 | Shaw | 206/498 |
| 3,985,227 | 10/1976 | Thyen et al. | 206/63.3 |

FOREIGN PATENT DOCUMENTS 2,532,992   12/1976   Germany .................. 206/63.3

*Primary Examiner*—William Price
*Assistant Examiner*—Joseph Man-Fu Moy
*Attorney, Agent, or Firm*—Charles F. Costello, Jr.

[57] ABSTRACT

A surgical suture label having a cut needle cover is disclosed which permits direct dispensing of the suture. An envelope having a tearing notch and a tear angle guideline across the face of the envelope is also disclosed. When the envelope is torn from the tear notch along the guideline, the suture in the label is exposed for direct dispensing.

6 Claims, 10 Drawing Figures

DIRECT DISPENSING PACKAGING OF SURGICAL SUTURES

BACKGROUND OF THE INVENTION

This invention relates to a cut suture label to permit direct dispensing of the suture and to a tearable suture envelope that can be torn from a tear notch across the face of the envelope so as to expose the label. A suture is a strand of material suitable for suturing, with or without a attached needle or needles, used for ligating or other surgical procedures.

The packaging of many commercial products is essential to the proper end use of the product and thus forms an integral part of the overall product design. The significance of packaging is most evident in the packaging of surgical sutures. It is essential that the package protect the product and maintain sterility throughout its period of potential use. Sutures may be stored in hospitals for several years, although the usual storage time is much shorter. It is essential that the package provide rapid and positive means of identification and release the product undamaged ready for use by the surgeon. There are many sizes of sutures, and many materials of construction such as catgut or polyglycolic acid for absorbables, silk, cotton, nylon, dacron, polyethylene, polypropylene, stainless steel, insulated stainless steel and other materials for use as nonabsorbables. There are several different needle types in common use including pointed straight, pointed curved, three cornered straight, three cornered curved, curved both regular and reverse cutting, and needles with side cutting edges of various types. The variations and combinations of each of these to meet the preference of many surgeons for different operative procedures means that the suture manufacturer needs to supply different suture combinations running into the thousands. The importance of positive identification and efficient, economical packaging can thus be readily appreciated.

It is also important to provide convenience to the user and limit the risk of accidently enclosing foreign items in the patient by limiting the number of extraneous packaging materials associated with use of the product in the operating theater. A count is often kept to ensure that each item is accounted for and removed from the operating field. Considering the ramifications of enclosing such material in the patient accidently during surgical procedures, it is obviously essential to minimize this hazard.

It is also important that the surgical package properly present the needles suitably oriented within the package so that the user can rapidly and reliably grip the needle with the needle forceps in the proper position for immediate use.

It is important also, to provide a standard packaging format for all suture materials to limit confusion on the part of the user during surgical procedures. Over the years a multitude of package styles has evolved that has detracted from user convenience and operating room efficiency. For purposes of storage in the hospital as well as economy of manufacture, it is highly desirable that as many suture combinations as feasible be packaged in a minimum number of different package styles and shapes and storage units. It is quite common to package 3 dozen identical sutures in a box. It is convenient to have most of the boxes about the same size and shape, so that the hospital may store them most conveniently. It is also convenient from the manufacturers stand point to be able to reduce his inventory of box sizes and to be able to use the same components for the maximum number of suture combinations in the product line.

It is essential that a package containing a surgical needle or needles, protect the suture from contact with the sharp point or cutting edge of the needle which could partially cut the suture or the package. Also the armed needle edges and point need to be protected so as to maintain their sharpness.

These requirements are so rigorous and of such importance that many different package designs have been tried. For example, see U.S. Pat. Nos. 3,959,947; 3,939,969; 3,876,068; 3,869,044; 3,728,829; 3,444,994; 3,202,273; 2,949,181; and Canadian Pat. No. 705,232. These patents are incorporated herein by reference. Generally, these patents disclose surgical suture or sutures packaged in a plastic or foil peelable envelope. Contained in the peelable envelope is an inner envelope or pouch, which is sterile. The suture strand has been formed into various configurations of coils and loops, contained in or on various retainers, labels, or reels, within the inner envelope. The suture is normally prepared for the surgeon by stripping the outer envelope and transferring the inner envelope by sterile forceps, or by projecting it across a sterile barrier, into the sterile areas of the operating room. The inner envelope is opened at the time of use.

The inner envelope and cut label of the present invention have advantages over these prior art patents. After tearing the inner envelope of the present invention, the lable can be folded and used without extracting it from the inner envelope. Access is provided from the inner envelope and folded label without removal of the label from the inner envelope. Thus, the proliferation of packaging materials within the immediate area of the operation or other surgical procedure is reduced. Further, besides direct access to the suture with or without needles, the suture is oriented within the label and inner envelope to allow immediate use when grasped by the needle holder. This is a desired operating room and surgical procedure technique, as it reduces the amount of time between extracting the suture from the label to its actual use as a suture. Still further, in most operations and surgical procedures, the materials used for the operation or surgical procedure are accounted subsequent to the operation or surgical procedure. The label and inner envelope of the present invention provide a readily identifiable and countable package.

SUMMARY OF THE INVENTION

The direct dispensing surgical suture label of this invention is a one-piece label. In the preferred embodiment, the label is divided by two score lines into three panels of approximately the same size. The center panel, which is the back panel when the label is folded, has recesses near the top and bottom to retain the suture strand. The center label contains a gapped and rounded corner on the side of the top portion adjacent to the needle cover described below. On the other corner, a cut is made forming a diagonal groove. On one side of the center panel is a suture strand cover which has a cut forming a diagonal groove on the top portion of the cover adjacent to the panel. A V-shaped groove is thus formed between the cover and the panel.

Along the top edge of the strand cover, notches are provided. Slits initiate from the bottom of the notches and terminate at dispensing holes. The length of the slit and the size of the hole is of such length and size as to easily accommodate a suture strand end. The holes are above the top recess of the center panel when the strand cover is folded over the center panel.

Strand retainer holes are located near the top and bottom portion of the strand cover. These holes will fit over the top and bottom recesses of the center panel when the strand cover is folded over the panel. A rectangular free space window is attached to the top retainer hole of the strand cover. The free space window allows grasping of the needle butt by the needle holders for direct dispensing. Surgical needle holding slits are located near the bottom corner portions of the strand cover to accommodate the pointed end of the needles.

On the other side of the center panel is a needle cover having a gapped and curved corner which is adjacent to the gapped and curved corner of the center panel. A U-shaped groove is thus formed between the needle cover and the panel. The other corner of the top portion of the needle cover is curved. Located on the top edge of the needle cover is a notch. An angular cut initiates from the notch and terminates in a score line perpendicular to the outer edge of the needle cover.

The recesses near the top and bottom portion of the center panel accommodate winding pins. When the pins are inserted in the recesses, the surgical suture strand could be wrapped in a FIG. 8 winding as described in FIG. 7. It is to be understood, however, that the surgical strand configuration can be any series of loops or coils that allow the strand to dispense freely without tangling from the label. The end of the surgical suture strand is then placed into the notch of the strand cover, passing through the slit and terminating at the dispensing hole.

The suture cover is then folded over the center panel along the score line. The strand retainer holes accommodate the winding pins. The suture cover holds the strand configuration on the center panel in place. The winding pins are retracted. If the end of the suture contains a needle, the needle point is placed in the needle holding slit.

The needle cover is then folded over the suture cover and center panel along the opposite score line.

When the portion of the needle cover between the notch and the curved corner on the outer edge of the needle cover is lifted, the end of the suture, with or without a needle is directly dispensed from the label.

In another embodiment, the surgical suture label described above could have locking slits on the outside edge of the needle cover and on the score line between the center panel and the strand cover. The needle cover would thus lock against the inside edge of the strand cover.

In another embodiment, a suture package containing the surgical suture label described above has been discovered. The suture package consists of a sealed envelope having a tearing notch and a tear angle guideline. The tear angle guideline initiates from the tearing notch. In the preferred embodiment the tear angle guideline terminates at a score line parallel to an outer edge of the sealed envelope. The depth of the tear notch, the length of the tear angle guideline and the length and proximity of the score line to the outer edge of the envelope is not critical as long as the portion of the needle cover is lifted and the end of the surgical suture is directly dispensed from the label.

Enclosed in the sealed envelope is the direct dispensing surgical suture label described above. When the sealed envelope is opened along the tear angle guideline, the flap formed by the notch and the curved corner on the outer edge of the needle cover is lifted. The end of the surgical suture is then directly dispensed from the label.

A double envelope suture package comprising a peelable outer envelope containing the sealed envelope described above as the inner envelope and enclosed in the inner envelope a direct dispensing surgical suture label of this invention is another preferred embodiment.

DESCRIPTION OF THE INVENTION

The present suture cover is, and remains, as a single piece within the inner envelope. In the preferred embodiment, the inner envelope which encloses and protects the suture in its label is notched and fits around the label so that it may be breached starting at the notch and torn open at the appropriate angle indicated, without tearing the envelope into more than one piece. The flap of the needle cover folds back during the tearing operation, or it may be aided with the needle holder, exposing the needle in its correct orientation which is grasped, and pulled gently and evenly, dispensing the suture. The present invention, and its advantages are also apparent from detailed descriptions of certain embodiments thereof which follow.

The three or four panel label is designed to protect the strand and envelope from damage by the needle. Various notches, holes, and slits, are specifically located on the various panels to hold the label closed, hold the needle(s) in proper orientation, aid dispensing, and aid grasping of the needle with needle holders.

The strand and needle label is preferably of a sterilizable paper, of 120 lb. weight, capable of withstanding alcoholic solutions, heat, steam, gas, or radiation sterilization without adverse effects. The paper may be coated with about one-half mil polyethylene so it is heat sealable. Such paper is known in the trade and is readily available. Sealing, if desired, may be by heat dies, or heat may be internally generated by ultrasonic means.

Figures 8, 9:
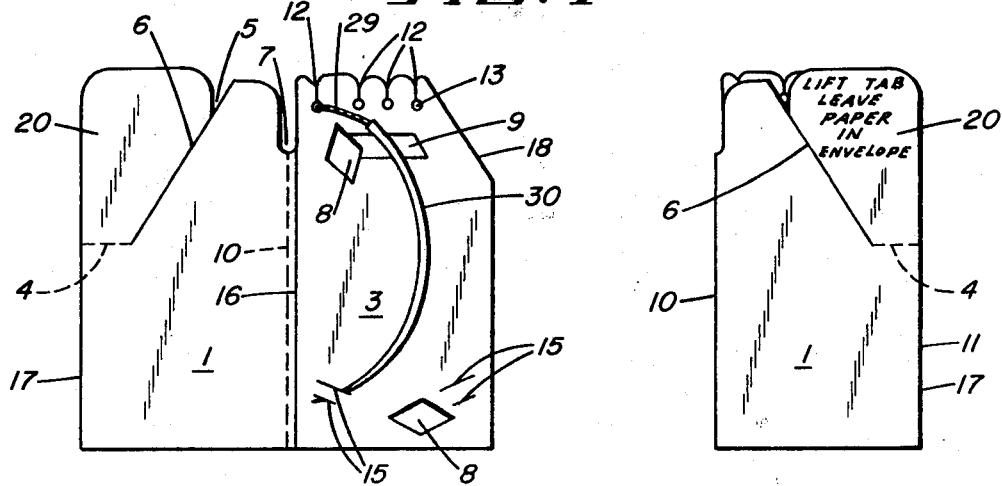
FIG. 8 shows the right panel folded over the center panel of FIG. 6 and showing the proper insertion of the needle into the slit.
FIG. 9 shows the left panel folded over the right and center panel of FIG. 8.

An important aspect of the present invention is having a tearable foil envelope that can be torn from a tear notch across the face so as to expose the label, with part of the label being unfolded or cut to permit direct dispensing of the suture — that is the suture, usually with a needle, may be pulled out of the label while the label remains in the envelope. Note the tear notch is at such a location that the label is retained in the foil envelope by an untorn corner. This avoids clutter in the operating room, as the entire label, and package assembly, though torn, is in a single piece. FIG. 9 of U.S. Pat. No. 3,876,068 teaches a tear notch for a surgical suture package. This patent is incorporated herein by reference.

The envelope and suture are both protected from armed edges of the needles. Preferably several types of needles can be packaged in the same label and envelope. Several needled sutures may be packaged in a single envelope, and preferably can be dispensed individually.

Figure 6:
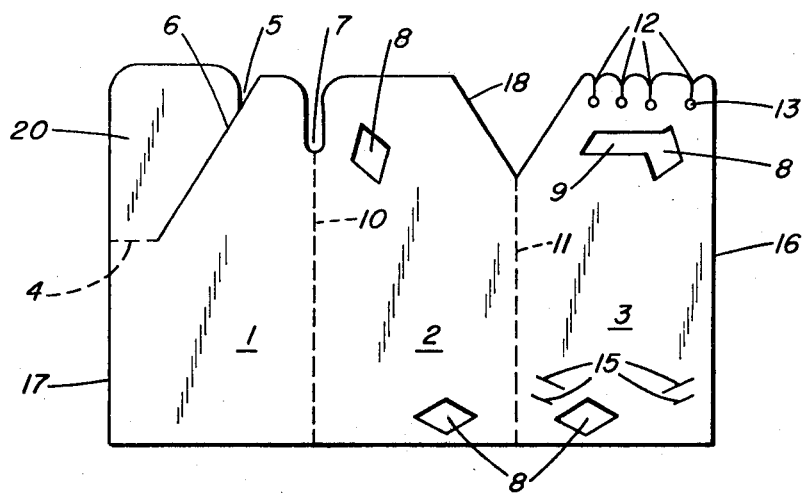
FIG. 6 is a front view of the suture label.

The label eg., in FIG. 6 is three panels without interlocks, with two apertures in the center panel for loop or 8 winding of the sutures. The right panel folds over the wound suture, has clearance slots for the winding pins, and several slots to hold the needle, and hold the suture. The suture is locked in a keyhole slot at the top of the right panel, and the needle may be in a slot in the right panel. The left panel folds over when the pins retract, and has a cut tab to be folded down to expose the needle when the foil envelope is torn.

The prepared suture is shown in FIG. 9. The suture is enclosed and sealed in a notched 21 inner envelope 25 which is shown in FIG. 2. The inner envelope in turn is sealed in a strippable outer envelope 31 shown in FIG. 1.

The inner envelope may conveniently be made of a moisture proof material such as a 25 Lb., calendered, bleached, pouch paper laminated with about a one-half mil of polyethylene to a metallic foil such as about a 1 mil aluminum foil which is again laminated to 1 mil polyethylene as an inner sealable layer. Such a material is disclosed in U.S. Pat. No. 3,728,839, incorporated herein by reference. Such material is essentially moisture proof so that synthetic absorbable sutures such as those of polyglycolic acid are protected from hydrolitic degradation. The same material may be used for the packaging of catgut sutures which are packaged with a desired quantity of water to maintain plasticity. Some sutures in which the moisture content is immaterial maybe also be packaged in the same material to maintain consistency of use and packaging standards.

Figure 1:
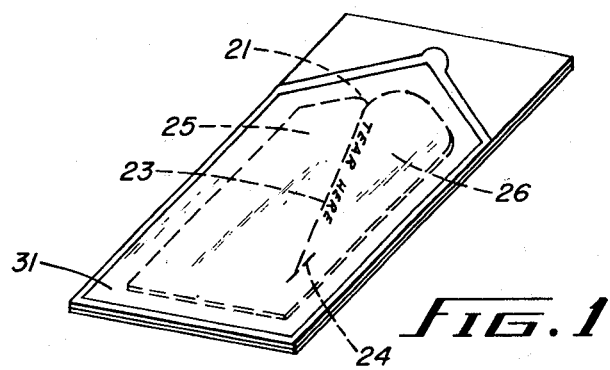
FIG. 1 shows a peelable outer envelope containing a tearable foil inner envelope.
Figure 2:
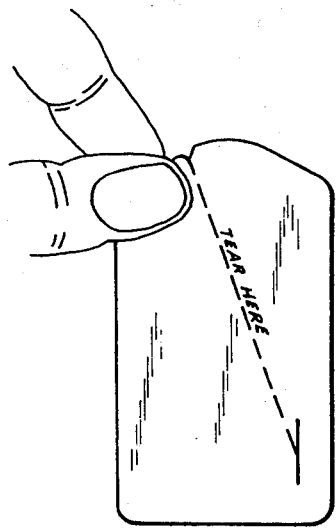
FIG. 2 shows the tearable inner envelope in position for use.
Figure 3:
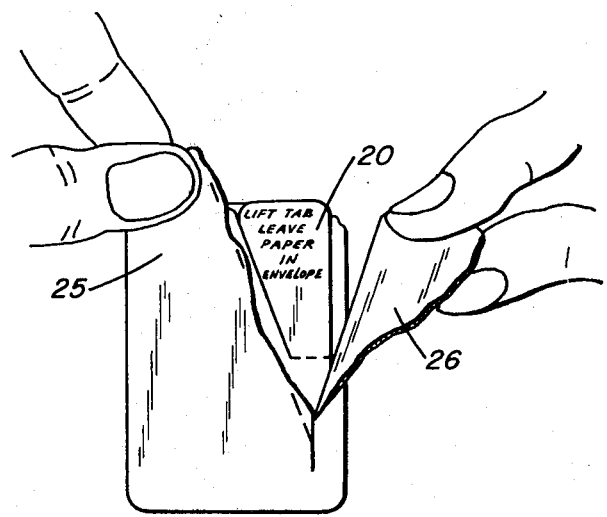
FIG. 3 shows the inner envelope being torn exposing the foldable panel of the label.
Figure 4:
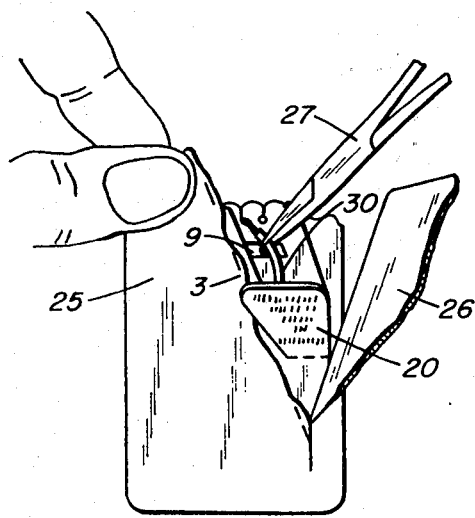
FIG. 4 shows the fully torn inner envelope and the partially folded panel of the label exposing a needle.

Referring to FIG. 1, the outer envelope 31 is peeled off. This would preferably be done prior to entry into the surgical area. Using the tearing notch 21 as a start the user may then open the inner envelope 25 by tearing the laminate longitudinally along the dotted guideline 23 to stop line 24 without detaching the torn portion 26. This action also lifts needle flap 20 shown in FIG. 3, exposing the needle as shown in FIG. 4. This action is enhanced by the specific size and shape of needle flap 20 in relation to the inner envelope. To aid the user in proper use of the package a tear arrow could be indicated on the dotted guideline 23.

FIG. 2 shows the inner envelope held in the position for use with the peelable outer envelope discarded. FIG. 3 shows the availability to lift of the needle flap 20 after the inner envelope 25 has been torn and the torn portion 26 folded back.

FIG. 4 shows the needle flap 20 folded back exposing the needle 30.

Referring to FIG. 4, the extended corner of the needle flap 20 in relation to the suture cover 3 ensures that the needle flap lifts and follows the torn portion of the envelope 26 shown in FIG. 3.

FIG. 4 shows the needle cover 1 with folded back needle flap 20 exposing the needle 30. The free space window 9 provides access by the needle holder 27.

Figure 5:
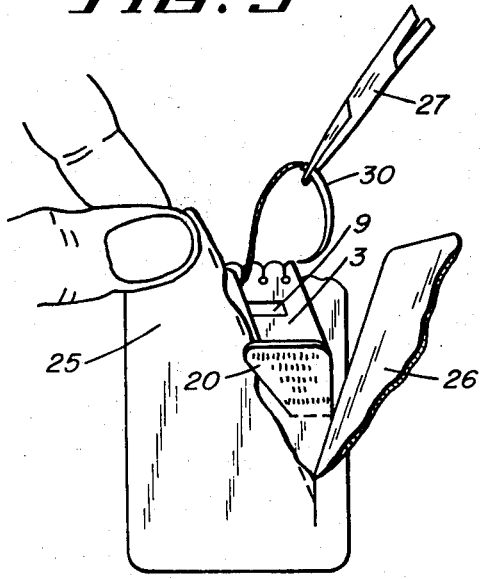
FIG. 5 describes one embodiment of the use of the direct dispensing package by removing the needle with needle forceps.

FIG. 5 shows the suture being dispensed from the label package described in FIG. 4. Due to specific design characteristics, the suture cover is securely locked within the opened portion of the envelope 25 and the entire package remains intact. Thus no additional materials or articles other than the needle and strand is added to the operating area. Related hazards are thus minimized and reconciliation is simplified.

FIG. 6 shows suture cover, cutout and scored from a sheet of 120 Lb. sterilizable paper. FIG. 6 may be scored with slits for closure, or may be coated with one-half mil polyethylene for heat sealing.

As shown in FIG. 6, the suture cover consists of a center panel 2 to which is attached by score lines 10, 11, a strand cover 3, and a needle cover 1. An optional panel may be attached by score line to the bottom of center panel 2, needle cover 1 or strand cover 3. Needle flap 20 is separated from needle cover 1 by cut line 6 and attached by scoreline 4. Needle cover 20 is formed with rounded corners forming notch 5. The rounded corner effect is maintained by notch 7. Holes 8 are provided to accommodate strand retainers required during coiling of the strand. Rectangular shaped cutout 9 forms a free space window to allow secure and convenient grasping of the needle. Notches 12 provide for entering the strand into holes 13 which anchor the needle in correct position and aid proper dispensing of the strand at time of use. Slits 15 are required to anchor needles of all sizes and shapes in the correct orientation and position across the free space window 9. Edges 16 and 17 complete the suture cover. V-groove 18 aids in packing the suture, prior to folding the strand cover 3.

Figure 7:
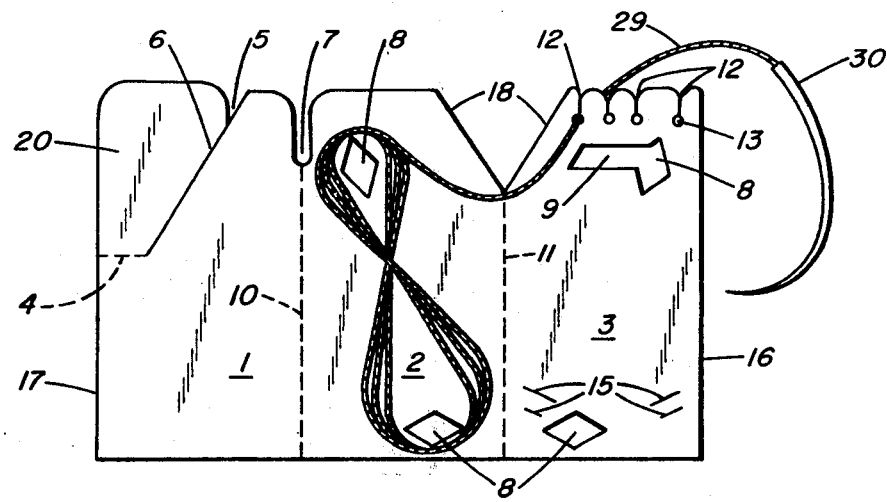
FIG. 7 is a preferred embodiment of the use of the suture label for wrapping the suture strand.
Figure 10:
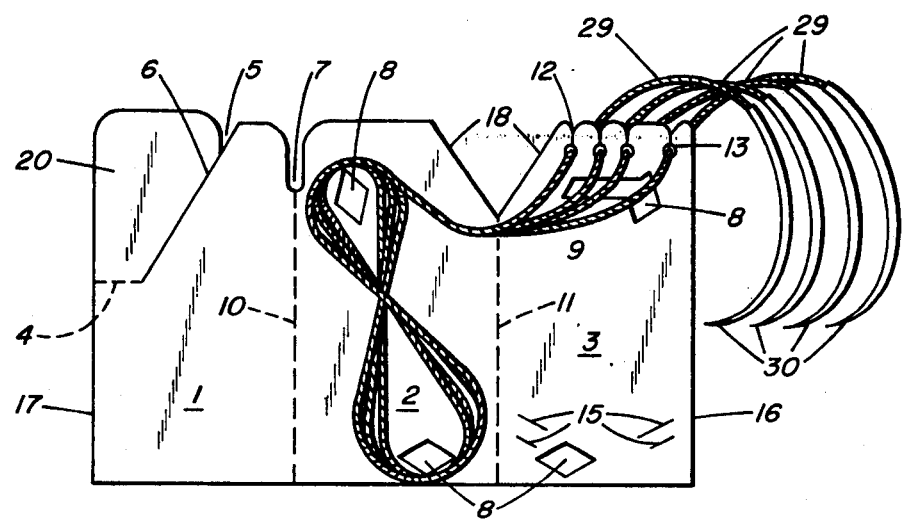
FIG. 10 is another preferred embodiment of this invention showing multiple surgical sutures used in the direct dispensing package.

FIG. 7 shows a figure eight looped coiled strand 29 with needle 30 in proper position prior to folding strand cover 3. The strand configuration can be any particular series of loops or coils that allow the strand to dispense freely without tangling. The relationship of the needled end of the strand to the rest of the coil is of no major significance. FIG. 10 is another preferred embodiment showing multiple strands 29 and needles 30.

FIG. 8 shows strand cover 3 folded in position over strand 29 shown in FIGS. 7 and 11 protecting the strand from damage by the cutting edge or point of the needle 30. Needle 30 is also shown in the appropriate dispensing slit 15. The positioning of curved needle 30 with the curve in a clockwise orientation is of importance since it allows the needle to be grasped with a needle holder at the correct place for use. It is then completely ready for immediate use by right handed surgeons, or it may simply be turned 180° for use by left handed surgeons.

FIG. 9 shows the relationship of needle flap 20 to the rest of the needle cover 1 and to the suture cover 3. Further, FIG. 9 shows the needle cover 1 folded over the needle thus protecting the inner envelope from damage by the cutting edge or the point of the needle. The needle cover 1 also protects the needle from being dulled by abrasion during processing or transit.

I claim:
1. A direct dispensing surgical suture label comprising:
   a center panel having recesses near the top and bottom portion, said recesses adapted to receive winding pins for winding a suture strand, a gapped and round corner on one side of the top portion, and a diagonal cut formed on the top portion of the other corner;

a suture strand cover having a diagonal cut on the top portion of said strand cover and adjacent said center panel forming a V-shaped groove between said panel and said cover, notches along the top edge, slits initiating from said notches and terminating at dispensing holes at the top portion of said cover, winding pin holes near the top and bottom portion of said cover aligned with said recesses, a rectangular free space window attached to the said top winding pin hole, and surgical needle holding slits near the bottom corner portions of said cover;

a needle cover having a gapped and curved corner adjacent to said gapped and rounded corner of said center panel such that a groove is formed between said needle cover and said panel, the other corner of the top portion being curved, a notch on the top edge of said needle cover, an angular cut intiating from said notch and terminating in a score line perpendicular to the outer edge of said needle cover;

whereby, when said suture cover is folded over said center panel and said needle cover is folded over said suture cover and a surgical suture is contained under the strand cover with the end of said suture placed in said dispensing hole and when the portion of said needle cover between said notch and said curved corner on the outer edge is lifted, the end of said suture is directly dispensed from said label.

2. A direct dispensing surgical suture label described in claim 1 having a heat sealable coating on one side.

3. A direct dispensing surgical suture label described in claim 1 having locking slits on the outside edge of said needle cover, and the adjacent edge of said center panel and said strand cover.

4. A direct dispensing surgical suture label described in claim 1 manufactured from stiff sterilizable stock.

5. A suture package consisting of a sealed envelope having a tearing notch and a tear angle guideline and enclosed therein a direct dispensing surgical suture label as set forth in claim 1, and in which said notch and said angular cut of said needle cover is adjacent to the tear notch and tear angle guideline of said envelope, such that when said envelope is opened, the flap formed by said notch and said angular cut of said needle cover is lifted.

6. A double envelope suture package comprising a peelable outer envelope containing a sealed envelope described in claim 5.

* * * * *